United States Patent
Kotsuka et al.

[11] Patent Number: 5,846,801
[45] Date of Patent: Dec. 8, 1998

[54] THERMOSTABLE LIPASE ISOLATED FROM *PSEUDOMONAS SOLANACEARUM*

[75] Inventors: Takashi Kotsuka; Keijitsu Tanaka, both of Chiba; Kazunori Sakimoto, Kanagawa, all of Japan

[73] Assignee: Novo Nordisk A/S, Bessvaerd, Denmark

[21] Appl. No.: 860,982

[22] PCT Filed: Feb. 27, 1996

[86] PCT No.: PCT/JP96/00454

§ 371 Date: Jul. 15, 1997

§ 102(e) Date: Jul. 15, 1997

[87] PCT Pub. No.: WO96/27659

PCT Pub. Date: Sep. 12, 1996

[30] Foreign Application Priority Data

Mar. 6, 1995 [JP] Japan .................................. 7-045803

[51] Int. Cl.⁶ ................................ C12N 9/20; C12N 1/20
[52] U.S. Cl. ........................................ 435/198; 435/253.3
[58] Field of Search ..................................... 435/198, 196, 435/253.3

[56] References Cited

U.S. PATENT DOCUMENTS 5,454,971  10/1995  Sakai et al. .............................. 510/320
5,480,787   1/1996  Negishi et al. .......................... 435/134

FOREIGN PATENT DOCUMENTS 6-153942  6/1994  Japan .
7-67636   3/1995  Japan .
8802775   4/1988  WIPO .

OTHER PUBLICATIONS

Sugihara et al., J. Biochem, vol. 112, pp. 598–603 (1992).

*Primary Examiner*—Jon P. Weber
*Assistant Examiner*—Susan Hanley
*Attorney, Agent, or Firm*—Steve T. Zelson; Elias J. Lambiris

[57] ABSTRACT

A thermostable lipase has been isolated from *Pseudomonas solanacearum* SD709 (FERM BP-5358) which has a mass of 32 kD by SDS-PAGE, enzymatic activity in a pH range of about 4–12, a pH optimum of 6.5–9.5 and a temperature optimum of 80°–90° C.

5 Claims, 5 Drawing Sheets

THERMOSTABLE LIPASE ISOLATED FROM *PSEUDOMONAS SOLANACEARUM*

CROSS-REFERENCE TO RELATED APPLICATIONS

This application is a 35 U.S.C. 371 national application of PCT/JP96/00454 filed Feb. 27, 1996 and claims priority under 35 U.S.C. 119 of Japanese application 7-45803 filed Mar. 6, 1995, the contents of which are fully incorporated herein by reference.

TECHNICAL FIELD

This invention relates to a novel lipase, a production method thereof and a microorganism producing the same, and more specifically, to a novel thermostable lipase showing high activity at high temperature which is produced by a bacterium belonging to *Pseudomonas solanacearum*, a microorganism producing the lipase and production method thereof.

BACKGROUND ART

A lipase is a general term of an enzyme which hydrolyze triglyceride, and has formerly been produced by extraction of internal organs of animals or by using microorganisms.

The lipase is extensively used as an enzyme for food processing to flavor dairy products, medicines as digestives, diagnosis of a blood lipid assay, industry in hydrolysis and improvement of fats and oils, and the like. The lipase is required to have various characteristics for each use, and a thermostable lipase is applied to a wide variety of fields and requested to be variously used.

In food processing, from a food-hygienic point of view, enzyme reaction at high temperature which is in low danger of bacterial contamination has been desired. In decomposition of fats and oils, application of the lipase has been considered. Hydrolysis of fats and oils is a process for producing fatty acid and glycerol which are materials of petrochemical products such as detergents, cosmetics and surface-active agents. At present the Colgate-emery method is mainly carried out which brings fats and oils into contact with steam at 250° to 260° C. and at 50 to 55 atmospheres, however, the method needs heavy facilities and is not appropriate for small-to-medium-scale production of soap, etc. Therefore, decomposition of fats and oils by a lipase has been investigated.

However, stearic acid (melting point: 67° to 70° C.) and palmitic acid (melting point: 63° to 640° C.) which constitute a variety of fats and oils are solid at ordinary temperature. For that reason, the reaction fats and oils must be reacted at the temperature above their melting points. Therefore, the lipase used for decomposition of fats and oils must have a high thermostability and a high reactivity at a high temperature.

Furthermore, in recent years, the lipase has been used for a solution of pitch troubles in paper-manufacturing industry (Japanese Examined Patent Publication No. Hei. 4-29794). The optimum temperature of the enzyme reaction conventionally adopted for a solution of pitch troubles is from 35° to 55° C. Since the conventional enzyme is inactivated above 70° C., the temperature of the enzyme reaction in the paper-manufacturing process is limited and the temperature must be controlled throughout the paper-manufacturing process in which the lipase is used. Also, the enzyme is not thermostable, which is one of the causes to inhibit the use of the enzyme for a solution of pitch troubles at the grinder treatment part.

At present, most of the well-known enzymes on the market used as a thermostable lipase are not adequate for the stability against heat and not practical. For that reason, a Japanese Unexamined Patent Publication No. Sho. 62-79782 proposed a thermostable lipase. However, the optimum temperature of the enzyme is from 60° to 70° C., and its thermostability is not sufficient, since the residual activity after treatment at 70° C. for 15 minutes is below 10%. Moreover, because the enzyme hardly acts on triacetin and tributyrin, its use is restricted to food-processing. A thermostable lipase derived from Rhizopus has been disclosed (Japanese Unexamined Patent Publication Number Sho. 59-156282), but the optimum temperature of the enzyme is 60° C. and the reactivity at a high temperature is not sufficient. Furthermore there are the reports of a lipase produced by *Pseudomonas mephitica* var.ii*polytica* which has the optimum temperature of 70° C. and is not inactivated by heat treatment at 60° C. for 14 hours (Japanese Examined patent Publication No. Sho. 50-25553) and that produced by *Pseudomonas fraji* which has an optimum temperature of from 75° to 80° C. and maintains 95% of the activity after heat treatment at 70° C. for 20 minutes (Agric.Biol.Chem. 41,1353–1358(1977)). However, the optimum temperature of these enzymes is not beyond 80° C., and also concerning thermostability, the activity thereof is reduced to some degree by treatment at 80° C. for 1 hour, and therefore they are not sufficiently satisfactory for thermostability.

PURPOSE OF THE INVENTION

As mentioned above, the well-known lipase is not sufficient for thermostability and reactivity at a high temperature, so that the opportunity to use the lipase practically has been little in the fields such as food-processing, industry and a paper-manufacturing process, and there have been problems of the temperature condition being restricted in the process using lipase.

Consequently, an object of the present invention is to provide a lipase having a high thermostability. Also, another object is to provide a production method thereof, the lipase having an excellent thermostability, and a bacterium producing the thermostable lipase.

DISCLOSURE OF THE INVENTION

Figure 1:
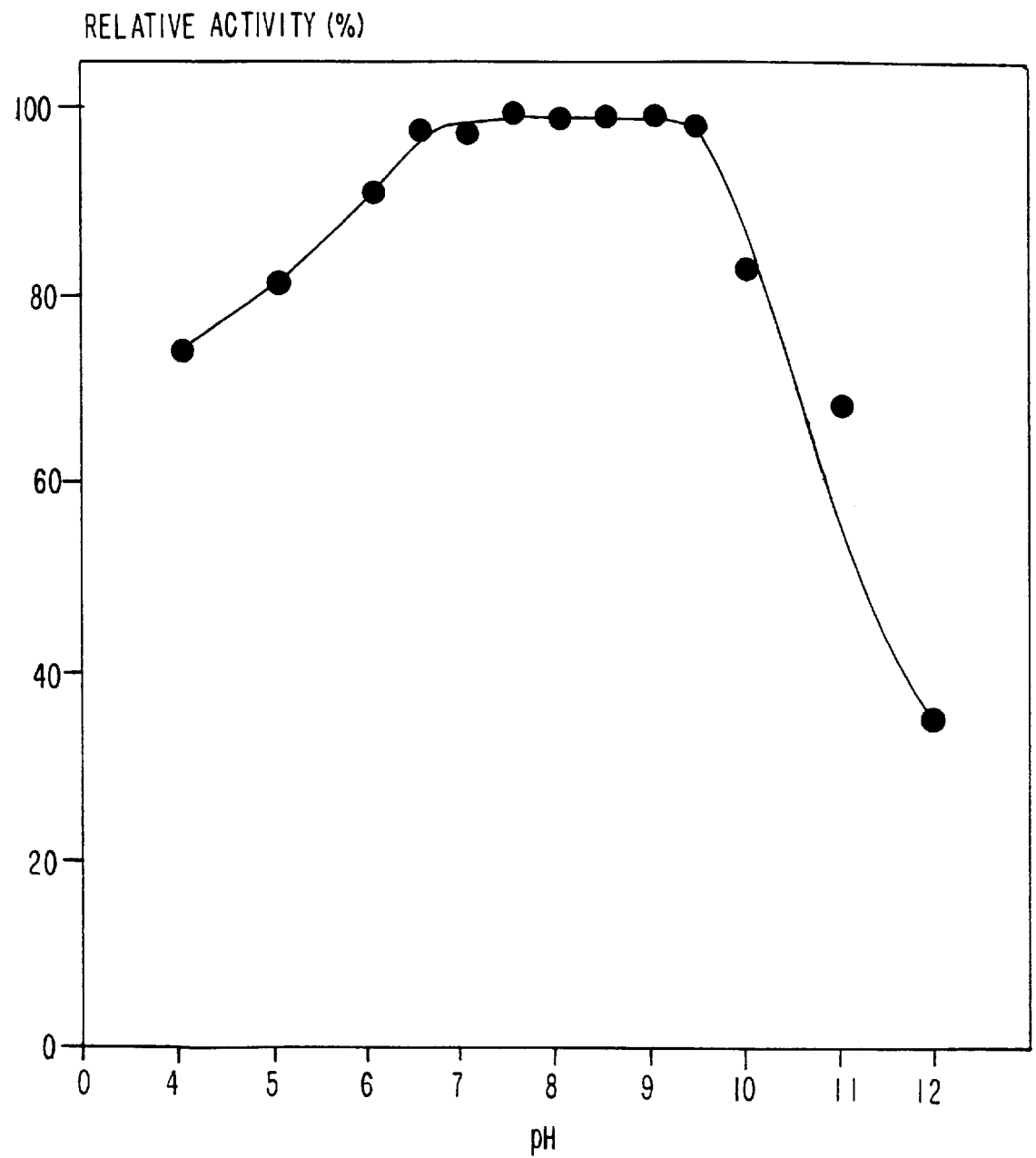
FIG. 1 is a graph showing the relationship between the reactive pH and the relative activity of the lipase produced by SD709.

The present inventors isolated, cultivated and screened a large number of microorganisms to obtain a lipase having a high thermostability and a high reactivity at a high temperature, and found out that the strain represented by *Pseudomonas solanacearum* SD709 (FERM P-14786), which had been isolated from the soil in Chiba prefecture in Japan, produces a novel thermostable lipase. Until now the lipase produced by numbers of strains has been known, but the thermostable lipase derived from *Pseudomonas solanacearum* has not yet been known. The inventors confirmed that the novel thermostable lipase is extremely effective for hydrolysis of lipids at a high temperature to achieve the invention. That is, the invention provides a lipase given below, a production method thereof and a microorganism producing the same.

1) A lipase having the active temperature of from 30° to 100° C. and the optimum temperature of from 85° to 100° C. determined using triolein emulsion as the substrate in the range of from 30° to 100° C., preferably, is a lipase having the properties below.

(1) Active pH and Optimum pH

The active pH is from 4 to 12 and the optimum pH is from 6.5 to 9.5, which are determined using triolein emulsion as the substrate in the pH range of from 4 to 12.

(2) Molecular Weight

The molecular weight determined by SDS-polyacrylamide gel electrophoresis is 32,000±2,000.

2) A lipase having the active temperature of from 30° to 100° C. and the optimum temperature of from 80° to 90° C. determined using triolein emulsion as the substrate in the range of from 30° to 100° C. in the presence of 5 mM EDTA, preferably, is a lipase having the properties below.

(1) Active pH and Optimum pH

The active pH is from 4 to 12 and the optimum pH is from 6.5 to 9.5 which are determined using triolein emulsion as the substrate in the pH range of from 4 to 12.

(2) Molecular Weight

The molecular weight determined by SDS-polyacrylamide gel electrophoresis is 32,000±2,000.

3) A lipase described in the 1) or 2) which is obtained from the culture medium of the bacterium which belongs to Pseudomonas, preferably, said bacterium belonging to Pseudomonas is *Pseudomonas solanacearum*.

4) A lipase described in 1) or 2) which is obtained from the culture medium of *Pseudomonas solanacearum* SD709 (FERM P-14786).

5) A bacterium described in 1) or 2) belonging to Pseudomonas which produces a lipase, preferably, *Pseudomonas solanacearum*, more preferably, *Pseudomonas solanacearum* SD709 (FERM P-14786), or a mycologically equivalent or their mutants.

6) A production method of a lipase which comprises cultivating the bacterium described in the 5) and obtaining the lipase described in 1) or 2) from the culture medium.

[Producing Strain]

The microorganism used for the production of the lipase according to the present invention is not especially limited so long as the bacterium can produce a lipase having the properties described below. Such a bacterium can be selected from preserved strains or microorganisms newly isolated from the natural world, a preferable bacterium is one belonging to Pseudomonas, and a more preferable one is belonging to *Pseudomonas solanacearum*. Further preferably, it is *Pseudomonas solanacearum* SD709 and its mycologically equivalents. In the present application, a mycologically equivalent mean strains having the almost same mycological properties. The equivalents naturally include natural or artificial mutant so long as they have the properties described below.

An example of the strains producing the novel lipase of the invention is SD709 which was isolated from the soil in Chiba prefecture in Japan by the present inventors.

The SD709 has the properties below.

| (1) Morphology: | Rod |
|---|---|
| (2) Gram Stain: | Negative |
| (3) Spore: | (−) |
| (4) Motility: | (+) |
| (5) Flagella: | Polar multiple flagella |
| (6) Oxidase: | Positive |
| (7) Catalase: | Positive |
| (8) OF test: | O |
| (9) Production of Fluorescent Pigment: | (−) |
| (10) Production of Water-Soluble Pigment: | (+) |
| (11) Cleavage of Protocatechuic Acid: | Ortho |
| (12) Arginine Dihydrase | Negative |
| (13) Growth at 41° C.: | Impossible |
| (14) Denitrification: | Positive |
| (15) Gelatin Liquefaction: | Positive |
| (16) Starch Decomposition: | Negative |
| (17) PHB Accumulation: | (+) |
| (18) Assimilation | |
| Glucose: | + |
| D-Xylose: | − |
| D-Ribose: | + |
| L-Rhamnose: | − |
| Levulinate: | + |
| Citraconate: | + |
| Mesaconate: | − |
| Adonitol: | − |
| 2,3-Butylene Glycol: | − |
| m-Hydroxybenzoic Acid: | − |
| Tryptamine: | − |
| Sucrose: | + |
| Caprylate: | + |
| L-(+)-Tartrate: | + |
| (19) Quinones: | Q-8 |

The classificatory properties of the bacterium having the mycological properties described above were compared with other strains by reference to Bergey's Manual of Systematic Bacteriology (1984) and, as a result, the strain was identified as *Pseudomonas solanacearum*. The strain was deposited in National Institute of Science and Human-Technology Agency of Industrial Science and Technology (1-1-3, Higashi, Tsukuba, Ibaragi, Japan) on Feb. 23, 1995 as P-14786 and has been transferred to the international deposit in accordance with the Budapest treaty since Dec. 28, 1995 as *Pseudomonas solanacearum* (Pseudomonas sp.) SD709 (FERM BP-5358).

A mutant producing a lipase which has the properties described below can be obtained by spontaneous or induced mutation from the strain above as the parent strain, and therefore the mutant can be used as the lipase producing bacterium. A conventional method to prepare the mutant is, for example, a method which comprises carrying out mutagenesis with an artificial means such as ultraviolet irradiation, treatment with N-methyl-N'-nitro-N-nitrosoguanidine (NTG), etc. for the parent strain, spreading that on nutrient agar containing oil such as olive oil, etc., selecting colonies in which the clear zones formed around the colonies are larger, cultivating them with a lipase production medium, and selecting the strain of excellent productivity.

[Production]

The lipase according to the invention is mainly obtained in the culture medium by cultivating the lipase producing bacterium. For a nutrient of the medium, usual ones are widely applicable. As carbon sources, an assimilative carbon compound or substance containing it can be used such as glucose, fats and oils, corn steep liqueur, Tween surface-active agents, etc. As nitrogen sources, a assimilative nitrogen compound or substances containing it can be used such as ammonium salt, nitrate, soy bean powder, meat extract, corn steep liqueur, pharmamedia. As inorganic salt, salt such as phosphate, magnesium salt, calcium salt, manganese salt is appropriately used.

The cultivation condition varies with the compositions of the culture medium, but the proper condition for production of the desired lipase is chosen. Usually, the cultivation temperature is from 10° to 35° C., preferably from 20° to 30° C., and the cultivation period is approximately from 8 to 100 hours, the cultivation is terminated when the production of the lipase reaches maximum. The preferable pH of the culture medium for production of the lipase is from 7 to 10. By means of such cultivation, the desired lipase is mainly produced extracellularly (in the culture medium).

[Separation and Purification Method]

To recover the lipase from the culture medium obtained in the above manner, a conventional method can be carried out by separation and purification to recover the lipase.

That is, the supernatant or filtrate obtained by separating the bacterial cells and solid medium from the culture medium is separated by well-known appropriate method such as filtration, centrifugation, and the separated solution, which may be concentrated or not, is treated by one or more of the separation or purification means such as salting-out in which the enzyme is precipitated by addition of soluble salt, organic solvent precipitation in which the enzyme or impurities is precipitated by addition of a hydrophilic organic solvent, adsorption/ desorption method using ion-exchange resin, gel filtration, spray drying with or without addition of stabilization, freeze drying, to give the lipase.

[Method of Enzyme Activity Assay]

The assay of the lipase activity was carried out by the assay using triolein-poly(vinyl alcohol) (PVA) emulsion as the substrate. The embodiment of the activity assay is described below.

The mixed solution consisting of 0.1 ml of the enzyme solution, 0.4 ml of 200 mM tris-buffer (pH 9.0) and 0.5 ml of triolein emulsion was heated in a test tube with an airtight stopper at 37° C. for 10 minutes to react, and the reaction was stopped by the addition of 0.2 ml of 1N hydrochloric acid as the reaction stopper. The triolein emulsion used here was prepared by adding 2.5 g of triolein to 10 ml of 2% aqueous solution of PVA (Poval PVA117 (trade name, Kuraray Co., Ltd.):Poval PVA205 (trade name, Kuraray Co., Ltd.)=9:1) and homogenizing it with ice cooling at 18000 rpm for 10 minutes. After the reaction was stopped, 2 ml of n-hexane, 2 ml of isopropyl alcohol and 1 ml of distilled water were added, vigorously stirred and allowed to stand, then, the oleic acid in a sample from the hexane layer was determined by TLC-FID method (Minagawa et al., Lipids, 18,732,1983). Unit (U) of activity was defined as the quantity of the enzyme generating 1 micro mole of oleic acid for 1 minute.

[Enzyme Property]

As an example of the lipase of the present invention, the properties of the lipase produced by *Pseudomonas solanacearum* SD709 mentioned above are described below.

(1) Action

It acts on glyceride and hydrolyzes its ester.

(2) Substrate Specificity

It widely hydrolyzes a variety of glyceride, ester, etc. The relative activity was determined by the enzyme activity assay described above using each glyceride-PVA emulsion as the glyceride substrate. The relative activities were 180 on tributyrin, 75 on olive oil, 90 on soy bean oil and 74 on cotton oil comparing with 100 in the decomposition power on triolein.

The decomposition ability on ester was determined by colorimetry with p-nitrophenol (OD405) generated from hydrolysis at pH 8.0 and 30° C. using p-nitrophenyl fatty acid ester as the substrate.

The relative activities were 170 on p-nitrophenyllaurate (pNPL) and 60 on p-nitorphenylvalerate (pNPV) comparing with 100 in the decomposition power on p-nitrophenylpalmitate (pNPP).

(3) Active pH and Optimum pH

They were determined by the enzyme activity assay described above using triolein emulsion as the substrate. The pH in the reaction was determined in various pH in the range of from 4 to 12. The mixed buffer consisted of 100 mM e-aminocapronic acid, 100 mM bis(2-hydroxyethyl) iminotris(hydroxymethyl)methane (bistris) and 100 mMN-tris(hydroxymethyl)methyl-3-aminopropanesulfonic acid (TAPS), and the pH of it was adjusted with hydrochloric acid or sodium hydroxide before use. The relationship between the reactive pH and the relative activity is shown in FIG. 1. The active pH determined in the range of from 4 to 12 was from 4 to 12, and the optimum pH was from 6.5 to 9.5.

(4) pH Stability

Figure 2:
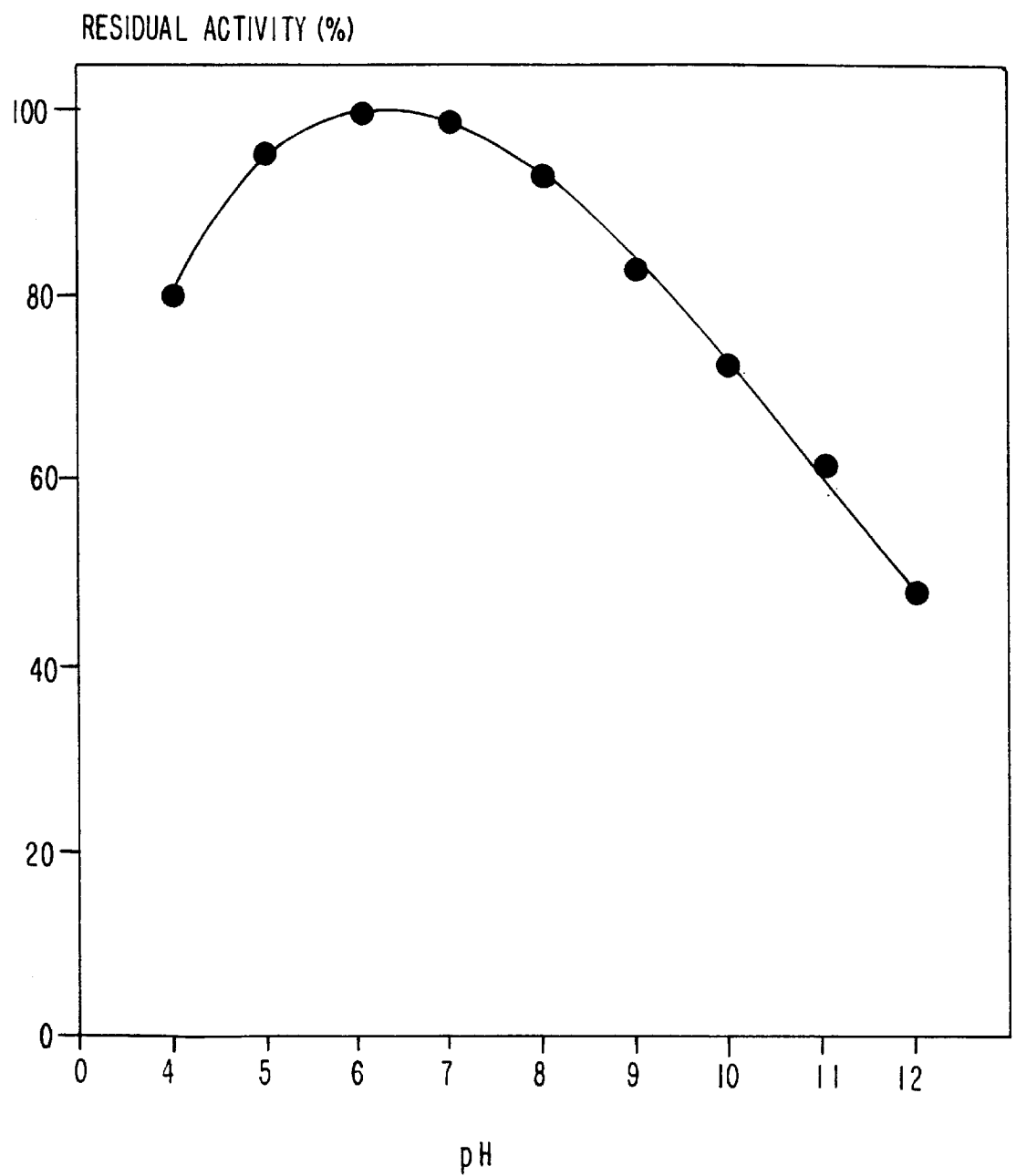
FIG. 2 is a graph showing the residual activity of the lipase produced by SD709 after it was maintained at varying pH at 37° C. for 1 hour.

The residual activity after treatment in varying pH in the range of from 4 to 12 at 37° C. for 1 hour was determined by the enzyme activity assay described above. The relationship between the treatment pH and the residual activity was shown in FIG. 2, and the residual activity in the pH range of from 4 to 11 is not less than 50%. The buffer used for the treatment comprised the followings; pH 4–5: acetic acid/sodium acetate, pH 6–7:phosphoric acid, pH 8–9:tris/hydrochloric acid, pH 10–12:glycine/sodium hydroxide.

(5) Active Temperature and Optimum Temperature

Figure 3:
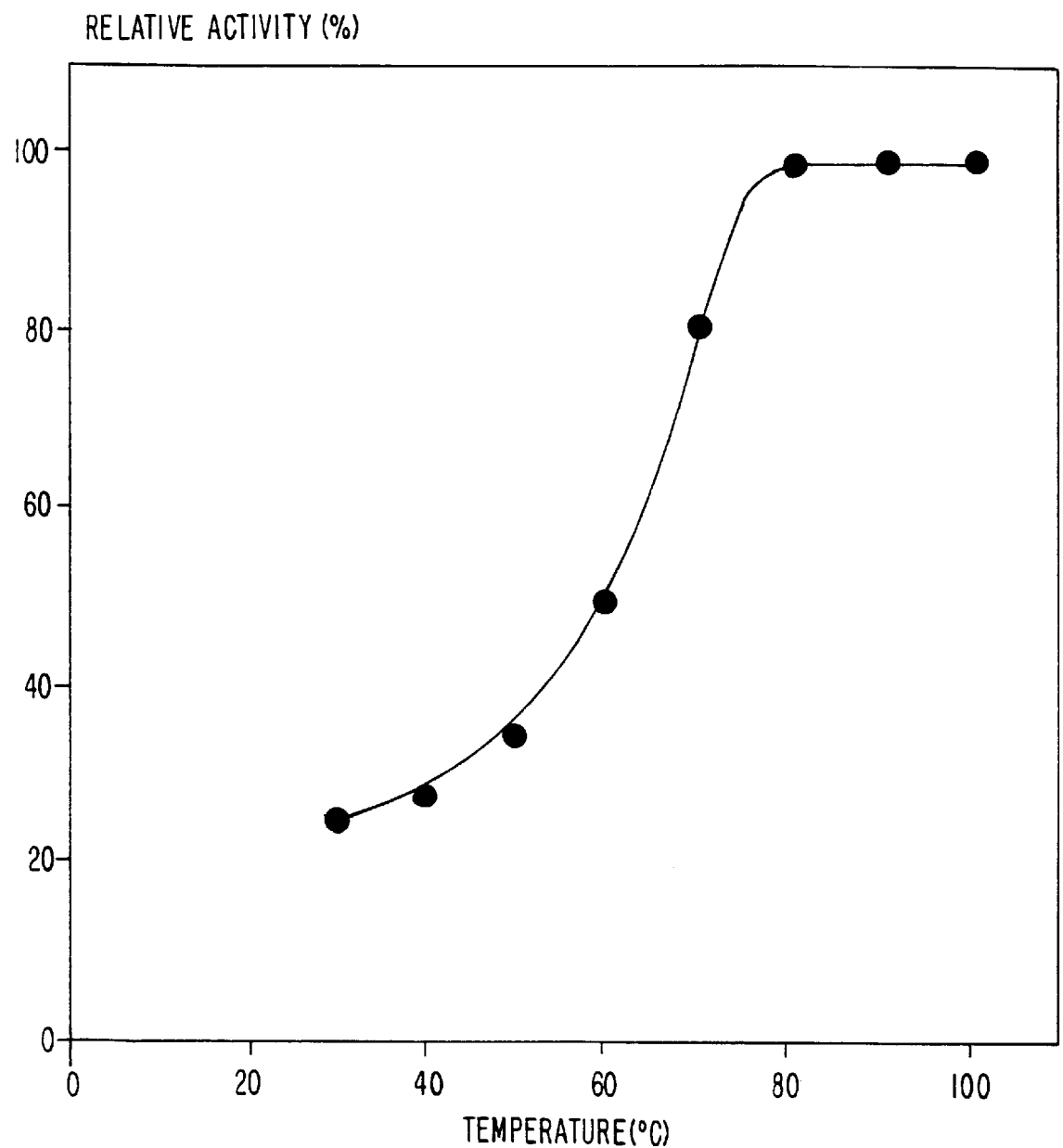
FIG. 3 is a graph showing the relationship between the reaction temperature and the relative activity of the lipase produced by SD709.

They were determined by the same enzyme activity assay described above except using triolein emulsion as the substrate and that the reaction temperature varied in the range from 30° to 100° C. The relationship between the reaction temperature and the relative activity was shown in FIG. 3. The active temperature determined in the range of from 30° to 100° C. was from 30° to 100° C. and the optimum temperature was from 85° to 100° C.

The active temperature and the optimum temperature were determined by the same enzyme activity assay described above except using triolein emulsion as the substrate in the presence of 5 mM ethylenediaminetetraacetic acid (EDTA) and that the reaction temperature varied in the range of from 30° to 100° C. The relationship between the reaction temperature and the relative activity was shown in FIG. 5. The active temperature determined in the range of from 30° to 100° C. was from 30° to 100° C. and the optimum temperature was from 80° to 90° C.

(6) Temperature Stability

Figure 4:
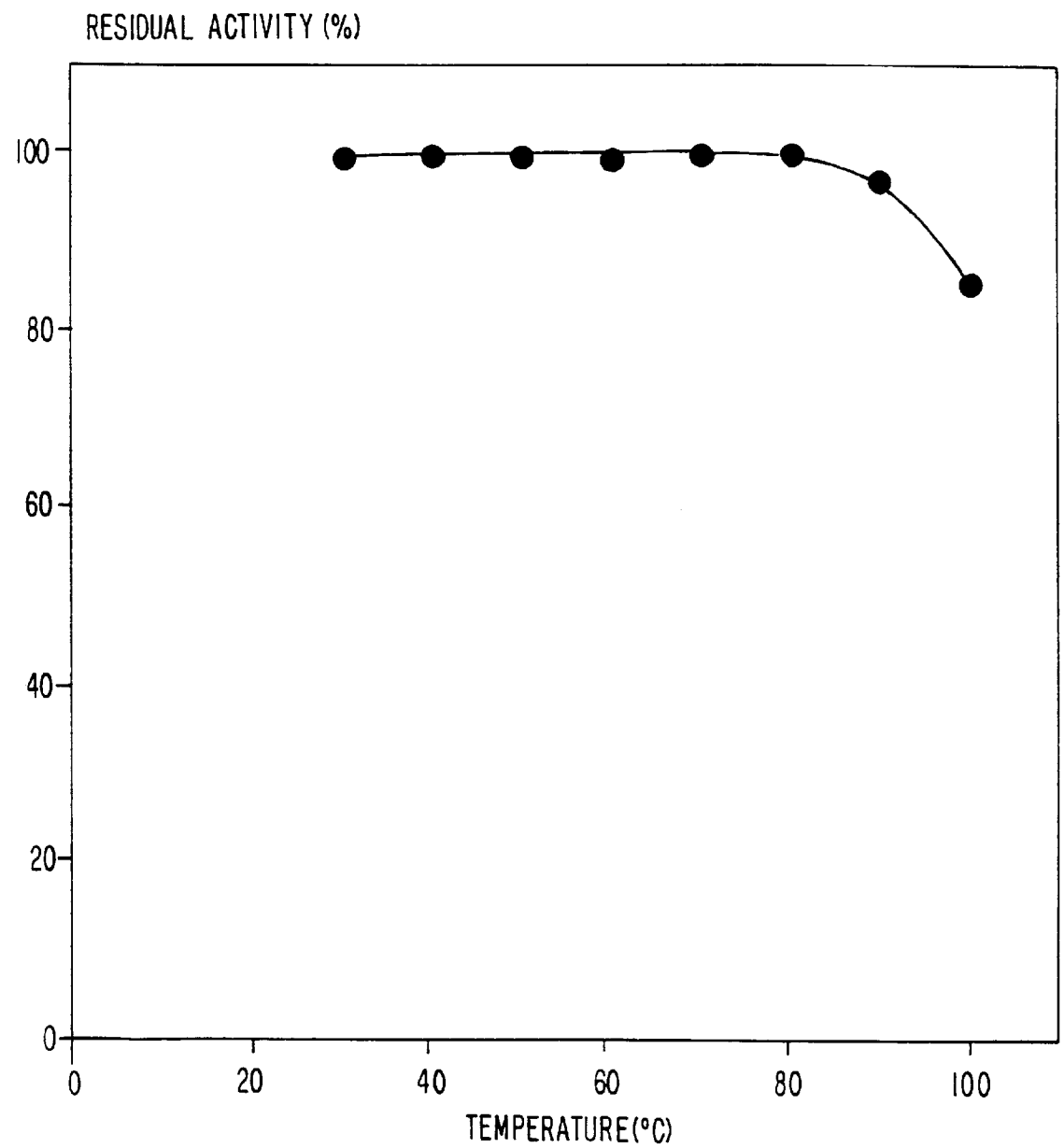
FIG. 4 is a graph showing the residual activity of the lipase produced by SD709 after it was treated at a variety of temperatures at pH 7 for 1 hour.

The residual activity after treatment at pH 7 and at varying temperature in the range of from 30° to 100° C. for 1 hour was determined by the enzyme activity assay described above. The relationship between the treatment temperature and the residual activity was shown in FIG. 4, and the residual activity after treatment at 80° C. was 100%.

(7) Molecular Weight

The molecular weight obtained by SDS-polyacrylamide gel electrophoresis is 32,000±2,000.

(8) Isoelectric Point

The isoelectric point obtained by SDS-polyacrylamide gel electrophoresis is 8.8±0.5.

BEST MODE FOR CARRYING OUT THE INVENTION

Now, the following examples are given to describe the present invention, but are not to be construed to limit the scope of the invention. The % in the following examples is based on weight unless otherwise indicated.

EXAMPLE 1
Cultivation of Lipase Producing Bacterium (SD709)

The liquid medium (2 ml) containing soy bean powder (2%), glucose (1%), diammonium hydrogen phosphate (0.1%), dipotassium hydrogen phosphate (0.5%), magnesium sulfate heptahydrate (0.1%) and sodium carbonate (0.3%) was put into a 18 mm diameter test tube and sterilized by autoclave at 121° C. for 20 minutes. It was inoculated with a loopful of Pseudomonas solanacearum SD709 and cultivated at 30° C. for 24 hours at 130 rpm. Thereafter, the bacterial cells were separated by centrifugation to give lipase solution. The lipase activity of the solution was 5 U/ml.

EXAMPLE 2
Cultivation of Lipase Producing Bacterium (SD709) and Recovery of Lipase The liquid medium (2 liter) containing soy bean powder (2%), diammonium hydrogen phosphate (0.1%), dipotassium hydrogen phosphate (0.5%), magnesium sulfate heptahydrate (0.1%), sodium carbonate (0.3%) and Tween 85 (1%) was placed on a 5 liter cultivation tub, and sterilized by autoclave at 121° C. for 20 minutes. It was inoculated with *Pseudomonas solanacearum* SD709 and cultivated at 30° C. for 24 hours at 1,000 rpm with aeration and stirring. Thereafter, the bacterial cells were separated by centrifugation to give lipase solution. The lipase activity of the solution was 20 U/ml.

From the lipase solution obtained above the precipitate of 20% to 30% fraction was obtained by ammonium sulfate precipitation. The precipitate was desalted by a conventional method, and freeze-dried to give lipase crude powder.

EXAMPLE 3
Purification of Lipase

The lipase crude powder obtained in Example 2 was dissolved in 10 mM tris/hydrochloric acid buffer (pH 7), and dialyzed against 10 mM tris/hydrochloric acid buffer (pH 7) containing 10% saturated ammonium sulfate, then treated by hydrophobic chromatography with Butyl-Toyopearl 650M (trade name, Tosoh Corporation) to give the active fraction. The active fraction was dialyzed against 10 mM tris/hydrochloric acid buffer (pH 8) containing 0.3 mM calcium chloride dihydrate and adsorbed to DEAE-Cellulofine A-800 (trade name, Seikagaku Corporation), ion-exchange chromatography resin, equilibrated in the same buffer, and eluted with sodium chloride solution to give the active fraction. The fraction was desalted and freeze-dried to give the purified enzyme.

The simplicity of the freeze-dried product was confirmed by polyacrylamide gel electrophoresis.

EXAMPLE 4
Activity at High Temperatures in the Presence of EDTA

Figure 5:
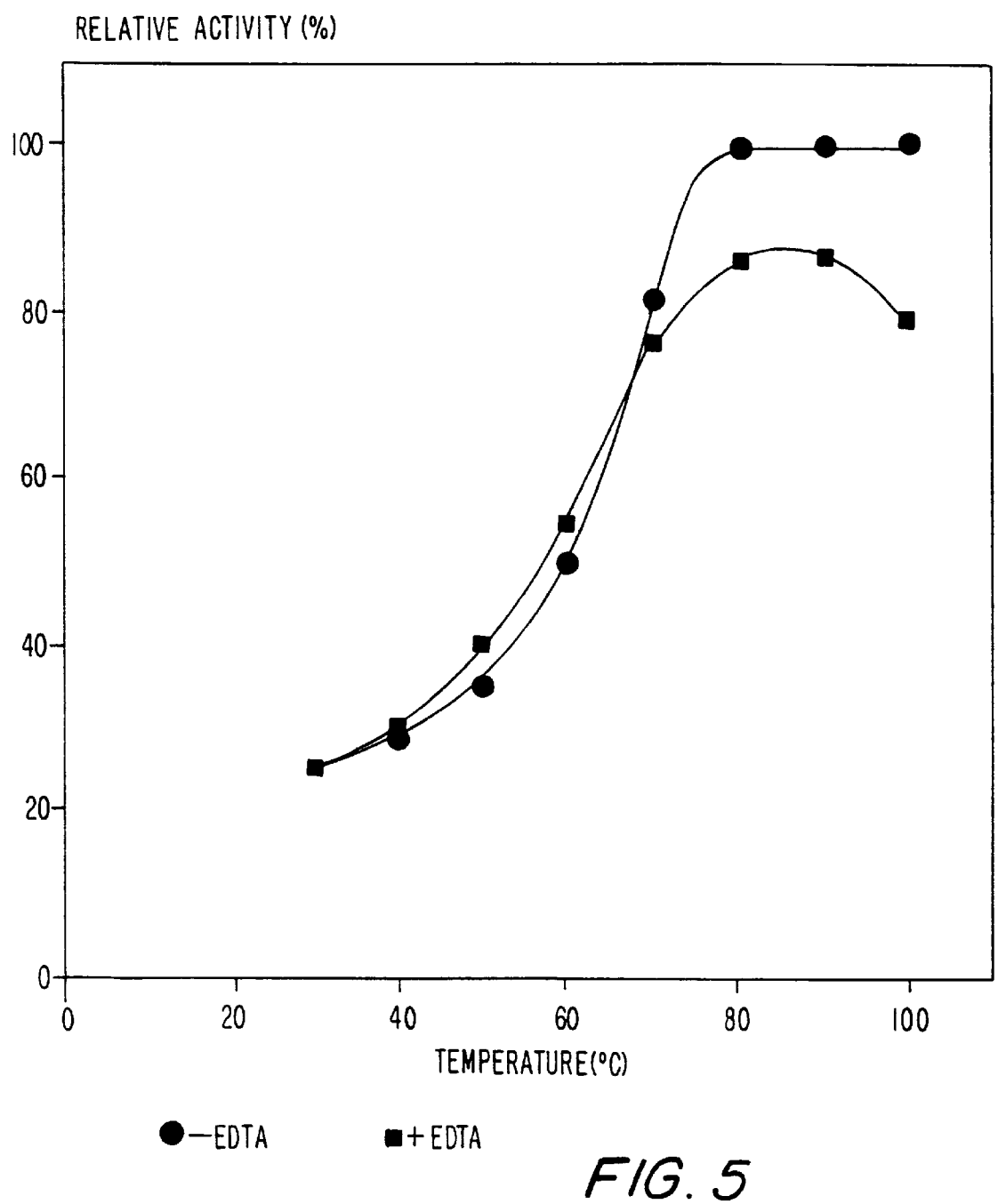
FIG. 5 is a graph showing the relationship between the reacting temperature in the presence and absence of EDTA and the relative activity of the lipase produced by SD709.

The activity of the lipase crude powder obtained in Example 2 was determined in the presence and absence of ethylenediaminetetraacetic acid (EDTA) using triolein emulsion as the substrate at varying temperature in the range from 30° to 100° C. The determination in the absence of EDTA is carried out by the same enzyme activity assay described above except the reaction temperature varied in the range from 30° to 100° C. And the determination in the presence of EDTA was carried out by the same way as that in the absence of EDTA except adding EDTA. The relationship between the relative activity comparing with 100 of the activity at 80° C. in the absence of EDTA and the reaction temperature is shown in FIG. 5. According to FIG. 5, the active temperature of the present lipase is from 30° to 100° C. and the optimum temperature of it is from 80° to 90° C. even in the presence of EDTA (in the absence of calcium ion), and it was observed that the lipase has sufficient activity at a high temperature.

INDUSTRIAL APPLICABILITY

The lipase of the present invention has a high thermostability, and therefore the activity can be exhibited in hydrolysis of lipids at a high temperatures, and the lipase can be widely used in the fields such as medicines, food-processing, cosmetic preparation, detergent compounding, treatment of waste water, decomposition of fats and oils, pitch control.

*Pseudomonas solanacearum* SD709 (FERM P-14786) of the present invention or its mycologically equivalent strain, or their mutants are useful for preparation of the present invention which efficiently produces the lipase.

We claim:

1. A purified lipase isolated from a strain of Pseudomonas, having:

(a) a temperature optimum of from 80° to 90° C., determined with triolein emulsion as a substrate in the presence of 5 mM EDTA;

(b) enzymatic activity in a pH range of about 4–12; and (c) a pH optimum at 6.5–9.5, determined using triolein emulsion as a substrate.

2. The lipase of claim 1, further having a molecular weight of 32,000±2,000 Daltons, determined by SDS-polyacrylamide gel electrophoresis.

3. The lipase of claim 1, wherein the Pseudomonas strain is *Pseudomonas solanacearum*.

4. The lipase of claim 3, wherein the Pseudomonas strain is *Pseudomonas solanacearum* SD709 (FERM BP-5358).

5. A process for producing the lipase of claim 1 by cultivating a *Pseudomonas solanacearum* SD709 bacterium, and recovering the lipase from the culture medium.

* * * * *

UNITED STATES PATENT AND TRADEMARK OFFICE
CERTIFICATE OF CORRECTION

PATENT NO. : 5,846,801
DATED : December 8, 1998
INVENTOR(S) : Kotsuka et al.

It is certified that error appears in the above-identified patent and that said Letters Patent is hereby corrected as shown below:

Col. 1, line 47: delete "640°C" and insert --64°C--
Col. 2, line 16: delete "var.ii*polytica*" and insert --var.lipolytica--

Signed and Sealed this

Seventh Day of December, 1999

Attest:

Q. TODD DICKINSON

*Attesting Officer*    Acting Commissioner of Patents and Trademarks